(12) United States Patent
Radermacher

(10) Patent No.: US 7,892,614 B2
(45) Date of Patent: Feb. 22, 2011

(54) POLYETHYLENE SQUEEZABLE POUCHES

(75) Inventor: Fabienne Radermacher, Obaix (BE)

(73) Assignee: Total Petrochemicals Research Feluy, Seneffe (Feluy) (BE)

( * ) Notice: Subject to any disclaimer, the term of this patent is extended or adjusted under 35 U.S.C. 154(b) by 541 days.

(21) Appl. No.: 10/573,952

(22) PCT Filed: Sep. 29, 2004

(86) PCT No.: PCT/EP2004/052347

§ 371 (c)(1),
(2), (4) Date: Jul. 24, 2008

(87) PCT Pub. No.: WO2005/030112

PCT Pub. Date: Apr. 7, 2005

(65) Prior Publication Data

US 2008/0272522 A1    Nov. 6, 2008

(30) Foreign Application Priority Data

Sep. 30, 2003   (EP) .................................. 03078044

(51) Int. Cl.
*B32B 1/08* (2006.01)
(52) U.S. Cl. .................... 428/35.2; 428/35.7; 428/35.5; 428/500; 604/403; 604/408
(58) Field of Classification Search .............. 428/35.2, 428/35.7, 35.5, 500; 604/403, 408
See application file for complete search history.

(56) References Cited

U.S. PATENT DOCUMENTS 4,332,122 A * 6/1982 Williams .................... 53/425
6,545,096 B1 * 4/2003 Honda et al. ................ 525/240

FOREIGN PATENT DOCUMENTS

JP          11019183 A * 1/1999

* cited by examiner

*Primary Examiner*—Michael C Miggins
(74) *Attorney, Agent, or Firm*—Tenley R. Krueger

(57) ABSTRACT

The invention relates to a process for producing polyethylene aseptic squeezable pouches. The invention also covers said pouches and their use for medical packaging applications.

8 Claims, 1 Drawing Sheet

1 (a)

1 (b)

1 (a)            1 (b)

2 (a)            2 (b)

POLYETHYLENE SQUEEZABLE POUCHES

Figure 1:
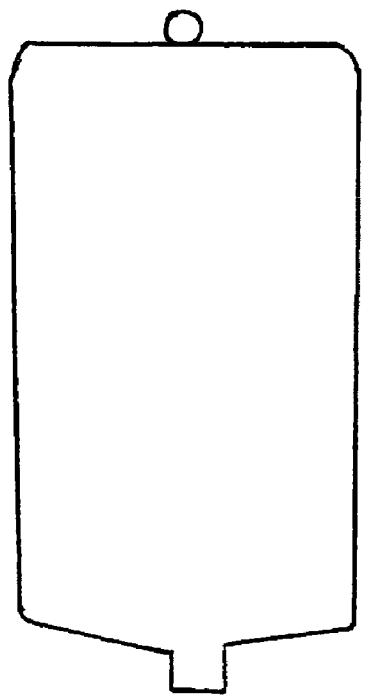
Figure 1:
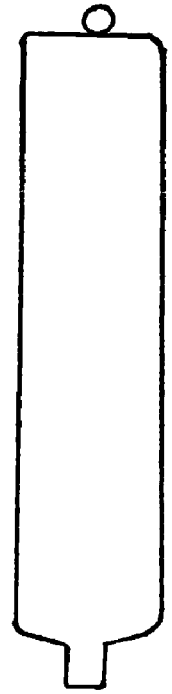

The present invention relates to a process for producing polyethylene blown filled sealed pouches having a high resistance to temperature, good optical properties and being easily squeezable. These can therefore be used as packaging for pharmaceutical and medical products especially for intravenous or parenteral solutions.

It is often highly desired in pharmaceutical and medical applications to get products free from contaminants. The blow/fill/seal process has emerged as a preferred method for aseptic packaging of liquid pharmaceutical and medical products. The blow/fill/seal process enables a plastic container to be molded, aseptically filled and hermetically sealed in one continuous, integrated operation. Further to the blow/fill/seal process, the sealed containers may, for the sake of safety, be sterilized by steam sterilization. This is particularly the case for intravenous liquids. It is well known that from an economic point of view, it is highly desired to avoid long sterilization time. The container must thus be able to be sterilized at sufficient high temperature but without causing any damage to the container.

Besides a resistance to high temperatures, the containers should also have good optical properties, particularly a good contact transparency and a high transmittance. Indeed, it is highly required that a visual inspection of the liquid can occur through the container in order to detect any possible contamination.

Moreover when the containers contain liquids such as for example intravenous solutions, it is desired that the container is sufficient flexible in order to automatically squeeze when solutions come out.

EP 0 601 631 relates to blown filled sealed containers made from a polyethylene composition comprising 50-80% of a linear low density polyethylene and 20-50% of a low density polyethylene prepared according to a radical high-pressure polymerization process. The containers are sterilized at a temperature of 117° C. Low density polyethylene resins are now adays used on the market for producing containers for pharmaceutical and medical products. However these containers are only resistant to temperature of 109° C. leading to high sterilization time when further sterilization is required after the blow/fill/sea l process.

There is thus still a need for producing polyethylene blown filled sealed containers that can be rendering aseptic by increasing their sterilization temperature without causing any distortion of the containers.

It is an object of the present invention to provide a process for producing aseptic blown filled sealed pouches.

It is another object of the present invention to provide blown filled sealed pouches that squeeze easily when liquids come out.

It is a further object of the present invention to provide blown filled sealed pouches with a high clarity transparence and a good transmittance.

The present inventor has found a process for producing aseptic blown filled sealed pouches, said process comprising the steps of:
a) extruding a metallocene catalyzed polyethylene having a density from 0.928 to 0.942 g/cm³ into a parison,
b) blowing the parison of step a into a pouch,
c) filling liquid into the pouch issued from step b,
d) sealing the filled pouch and
e) sterilizing said pouch at minimum 118° C.

For medical applications, such as for intravenous solutions, sterile air may be used in step b) of the process.

The present inventor has found that the process according to the invention leads to one or more of the objects of the invention.

The metallocene catalysed polyethylene (mPE) used in the present invention is copolymer of ethylene with a comonomer selected from the group consisting of propylene, 1-butene, 1-hexene, 1-octene or 4-methyl-1-pentene, the preferred comonomer being 1-hexene.

The density of the mPE used in the present invention can be regulated by the amount of comonomer injected in the reactor. The density of the mPE may range from 0.928 g/cm³ to 0.942 g/cm³, preferably from 0.930 g/cm³ to 0.940 g/cm³, most preferably from 0.932 g/cm³ to 0.936 g/cm³. In this specification, the density of the polyethylene is measured at 23° C. using method ASTM D 1505.

The melt index $MI_2$, according to ASTM D 1238 condition 2.16 kg/190° C., of the mPE used in the present invention can be regulated by the amount of hydrogen injected in the reactor. The melt index of the mPE may range from 0.3 g/10 min to 2.5 g/10 min, preferably from 0.5 g/10 min to 1.5 g/10 min and most preferably from 0.7 g/10 min to 1.05 g/10 min.

Preferably, the mPE resin used in the present invention has a rheological long-chain branching index, LCBI, such as defined by R. N. Shroff and H. Mavridis in Macromolecules 2001, 34, 7362-7367 by the equation:

$$LCBI = \frac{\eta_0^{0.179}}{4.8[\eta]} - 1$$

where $\eta_0$ is the limiting, zero-shear viscosity at 190° C. and $[\eta]$ is the intrinsic viscosity in trichlorobenzene at 135° C.

The LCBI is calculated from the best fitting by least squares analysis of the rheological curve (complex viscosity versus frequency) as described in U.S. Pat. No. 6,114,486 with the following generalized Cross equation, i.e.

$$\eta = \eta_0/(1+(\gamma t_0)^n)$$

wherein $\eta$ and $\gamma$ are the measured viscosity and shear rate data respectively, $\eta_0$ is the zero-shear viscosity, $t_0$ is the characteristic relaxation time of the material, n is the power law index of the material characterizing the shear thinning behavior of the material. The dynamic rheological analysis is performed at 190° C. under nitrogen and the strain amplitude is 10% according to ASTM D 4440.

The LCBI of the mPE used in the present invention is greater than 0.14, preferably greater than 0.50, more preferably greater than 1, most preferably greater than 2.

The catalyst system used to produce the mPE required by the present invention comprises a metallocene component, preferably a bridged metallocene component. The metallocene component may be any metallocene component of the general formula:

$$R_n''(C_pR'_k)_2MQ_{Z-2}$$

wherein $(C_pR'_k)$ is a cyclopentadienyl or substituted cyclopentadienyl, each R' is the same or different and is hydrogen or a hydrocarbyl radical such as alkyl, alkenyl, aryl, alkylaryl or arylalkyl radical containing from 1 to 20 carbon atoms and/or two carbon atoms are joined together to form a $C_4$-$C_6$ ring, R" is a substituted or unsubstituted $C_1$-$C_4$ alkylidene radical, a dialkyl or diaryl germanium or silicon or siloxane, or a alkyl phosphine or amine radical bridging two $(C_pR'_k)$ rings, n can be zero or 1, preferably n is 1, Q is a halogen or a hydrocarbyl radical having from 1 to 20 carbon atoms such as aryl, alkyl, alkenyl, alkylaryl or arylalkyl radical or a hydrocarboxy radical having 1-20 carbon atoms or halogen and can be the same or different from each other, k is either 4 when n is 1 or 5 when n is zero, Z is the valence of the transition metal and M is a group 4b, 5b or 6b transition metal, preferably a group 4b transition metal, most preferably zirconium.

Preferably, the metallocene catalyst is a substituted or unsubstituted bis indenyl zirconium dichloride, preferably a bridged substituted or unsubstituted bis indenyl zirconium dichloride, more preferably a bridged bis tetrahydro indenyl zirconium dichloride.

According to one preferred embodiment, the bridged metallocene catalyst is ethylene bis(4,5,6,7-tetrahydro-1-indenyl) zirconium dichloride.

The metallocene may be supported and activated according to any method known in the art.

The metallocene catalyst utilized to produce the polyethylene required by the present invention can be used in gas, solution, slurry or high-pressure polymerizations. Preferably, slurry polymerization is used to prepare the mPE required by the present invention.

Standard additives such as antioxidants, antistatic, antifog, anti-UV and antiblocking or slip additives may also be added to the resin. If desired, processing aids can also be added.

The temperature of the sterilization of the pouch is at minimum 118° C. Preferably the sterilization is conducted at 119° C., more preferably the sterilization is conducted at 119° C. during 15 minutes.

The present invention further provides squeezable pouches produced according to the process of the invention. Preferably, the pouches produced have a transmittance of at least 95% when measured according to standard method ASTM D 1003 and a haze of less than 35%, preferably less than 32% when measured according to standard method ISO 14782. The pouches are also characterised by an excellent contact transparency.

The present invention still further provides the use of the pouches produced according to the process of the invention for medical packaging applications

EXAMPLES

A metallocene-catalyzed polyethylene resin (R1) was used to prepare aseptic blown, filled, sealed pouches. The metallocene catalyst used was the bridged metallocene ethylene bis(4,5,6,7 tetrahydro-1-indenyl) zirconium dichloride. The polymerization of the resin R1 used in the process of the present invention was carried out in a liquid-full slurry loop reactor. Ethylene was injected with 1-hexene together with the catalyst. Isobutane was used as diluent. The polymerization conditions wherein C2 is ethylene, C6 is 1-hexene, Iso C4 is isobutene, TIBAL is triisobutylaluminium were as follows:

C2 feed (Kg/h): 3900,
C6/C2 feed ratio (kg/T): 22,
H2/C2 feed ratio (g/T): 42,
Iso C4 feed (kg/h): 1940,
TIBAL conc (ppm): 100-200,
Polymerisation temperature: 90° C.
Comparative pouches were produced by using:
1. A polyethylene resin sold by Atofina under the name Finathene® HF513 prepared with a chrome catalyst (R2).
2. A polyethylene resin sold by Basell under the name Lupolen® 3040D (R3).
3. A polypropylene resin sold by Atofina under the name Atofina® polypropylene 3020SM3 (R4)

The MI2 has been measured as defined above. The MFI has been measured following the method of standard test ASTM D 1238, under a load of 2.16 kg and at a temperature of 230° C. The properties of these resins are summarized in table 1.

TABLE 1

| Resin | Density g/cm³ | MI2 g/10 min 190° C. | MFI g/10 min 230° C. |
|---|---|---|---|
| R1(example) | 0.935 | 0.9 | — |
| R2(comparative) | 0.934 | 0.15 | — |
| R3(comparative) | 0.930 | 0.3 | — |
| R4(comparative) | 0.900 | — | 1.8 |

The resin R1 presented a long-chain branching index, LCBI, of 0.60. The LCBI of R1 was determined by fitting the generalized Cross equation on the complex viscosity reported according to ASTM D 4440.

Pouches Preparation.

All the resins were, in one process cycle, extruded into a parison, blown into pouches, filled with water and sealed. The blown filled sealed process occurred on a Rommelag equipment. The pouches were afterwards sterilized at 119° C. in an autoclave during 15 minutes. The pouches produced had a contenance of 500 ml. The other characteristics are mentioned in table 2.

TABLE 2

| Pouches | Composition | Weight (gr) | Thickness (mm) |
|---|---|---|---|
| P1(example) | R1 | 18.5 | 0.45 |
| P2(comparative) | R2 | 28 | 0.5 |
| P3(comparative) | R3 | 21.9 | 0.5 |
| P4(comparative) | R4 | 19.7 | 0.5 |

Pouches Properties.

All the pouches were tested for their resistance to a temperature of 119° C. by detecting if leakage of water occurred when the pouches were maintained at this temperature for 15 minutes.

Figure 2:
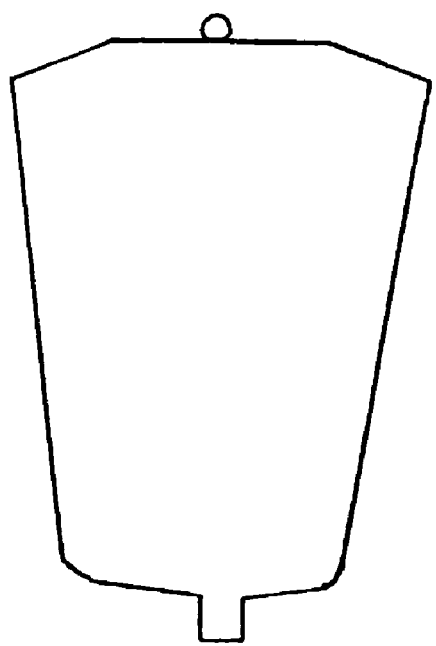
Figure 2:
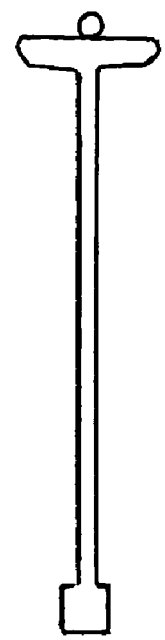

The pouches were further tested for their squeezable behavior. The pouch produced according to the process of the invention automatically squeezed when the liquid came out. In FIG. 1, we can see the front view (1a) and profile view (1b) of a filled sealed pouch before water came out. In FIG. 2, we can see the front view (2a) and profile view (2b) of a sealed pouch after water has come out.

The pouches were also tested for their optics especially, the transmittance, haze and contact transparency. The transmittance has been measured according to standard method ASTM D 1003. The haze has been measured according to standard method ISO 14782. All the results are displayed in table 3.

TABLE 3

| Pouches | Temperature resistance | Transmittance (%) | Haze (%) | Contact transparency | Squeezable behavior |
|---|---|---|---|---|---|
| P1 (example) | No leakage | 95 | 31 | Excellent | Excellent |
| P2 (compara- | leakage | 89 | 78 | Poor | Very good |

TABLE 3-continued

| Pouches | Temperature resistance | Transmittance (%) | Haze (%) | Contact transparency | Squeezable behavior |
|---|---|---|---|---|---|
| tive) | | | | | |
| P3 (comparative) | leakage | 91 | n.m. | Very good | Very good |
| P4 (comparative) | No leakage | 93 | n.m. | Excellent | Poor | n.m: not measured

The pouches produced according to the invention combine a good resistance to high temperature, excellent optics and an excellent squeezable behavior.

The invention claimed is:

1. A sterilizable container comprising:
   a) a liquid fill pouch produced by the process of:
      i) extruding a single polymer consisting essentially of a metallocene catalyzed ethylene polymer having a density within the range of 0.928-0.942 g/cm$^3$ into a parison;
      ii) blow molding said parison into a pouch;
      iii) introducing a liquid into said pouch;
      iv) sealing said pouch containing said liquid to produce a sealed liquid containing pouch; and
   b) said pouch characterized by retaining its integrity at a sterilization temperature of 118° C.

2. The container of claim 1 wherein said metallocene catalyzed ethylene polymer is a copolymer of ethylene and a $C_3$-$C_8$ alpha olefin comonotner.

3. The container of claim 1 wherein said ethylene polymer is a copolymer of ethylene and 1-hexene.

4. The container of claim 1, wherein the metallocene comprises ethylene bis(4,5,6,7-tetrahydro-1-indenyl)zirconium dichloride.

5. The container of claim 1 wherein the wall of said pouch has a transmittance of at least 95% as measured in accordance with ASTM D 1003.

6. The container of claim 5 wherein the wall of said pouch has a haze of less than 35% when measured according to standard ISO 14782.

7. The container of claim 6 wherein the wall of said pouch has a haze of less than 32%.

8. A sterilizable container comprising:
   a) a liquid fill pouch produced by the process of:
      i) extruding a single polymer consisting essentially of a metallocene catalyzed ethylene polymer having a density within the range of 0.928-0.942 g/cm$^3$ into a parison, wherein the metallocene comprises ethylene bis(4,5,6,7-tetrahydro-1-indenyl) zirconium dichloride;
      ii) blow molding said parison into a pouch;
      iii) introducing a liquid into said pouch;
      iv) sealing said pouch containing said liquid to produce a sealed liquid containing pouch; and
   b) said pouch characterized by retaining its integrity at a sterilization temperature of 118° C.

* * * * *

UNITED STATES PATENT AND TRADEMARK OFFICE
CERTIFICATE OF CORRECTION

| | |
|---|---|
| PATENT NO. | : 7,892,614 B2 |
| APPLICATION NO. | : 10/573952 |
| DATED | : February 22, 2011 |
| INVENTOR(S) | : Fabienne Radermacher |

Page 1 of 1

It is certified that error appears in the above-identified patent and that said Letters Patent is hereby corrected as shown below:

Claim 1, Column 5, Line 28, --scaling--, should be changed to "sealing".

Claim 2, Column 6, Line 3, --comonotner--, should be changed to "comonomer".

Signed and Sealed this
Twenty-fourth Day of May, 2011

David J. Kappos
*Director of the United States Patent and Trademark Office*